US00PP09267P

United States Patent [19]

Jessel, Jr.

[11] Patent Number: Plant 9,267

[45] Date of Patent: Aug. 29, 1995

[54] CARNATION PLANT NAMED 'CFPC COTILLION'

[75] Inventor: Walter H. Jessel, Jr., Salinas, Calif.

[73] Assignee: California Florida Plant Co., L.P., Salinas, Calif.

[21] Appl. No.: 315,132

[22] Filed: Sep. 29, 1994

[51] Int. Cl.[6] ..... A01H 5/00

[52] U.S. Cl. ..... Plt./70.5

[58] Field of Search ..... Plt. 70.5, 70.1, 70.2, Plt. 70.6

*Primary Examiner*—James R. Feyrer

*Attorney, Agent, or Firm*—Christie, Parker & Hale

[57] ABSTRACT

A new dwarf carnation plant suitable for growing in pots producing light pink and picotee wine-red flowers.

1 Drawing Sheet

SUMMARY OF THE INVENTION

The present invention relates to a new and distinct dwarf variety of carnation plant which was originated by me in a controlled breeding program by my crossing as seed and pollen parents, two proprietary, unnamed and unpatented seedlings of my creation. The varietal denomination of this new carnation is 'CFPC Cotillion'.

Among the novel combination of characteristics possessed by the new variety which distinguishes it are dwarf growth habit not requiring application of growth retardants, tolerance to temperatures as high as 120° F. and as low as 10° F. and ability to produce flower buds that will open in a home environment with moderate light conditions. Flowers of the new variety are of an attractive light pink and picotee wine-red coloration.

Asexual reproduction by propagation by side shoot cuttings of the new variety as performed in Salinas, Calif., shows that the foregoing and other distinguishing characteristics come true to form and are established and transmitted through succeeding propagations.

Unlike preceding pot carnations, i.e., Lillipots (Sakata), Rocky Mountain Series (Goldsbury C.S.U.), and Knight Series (Goldsmith Seed Co.), CFPC pot carnations were selected and bred from indoor cut-types and are best grown under cover. The Lillipots etc. were bred from outdoor garden-types and species and are best grown outdoors. The CFPC pot varieties are dwarf due to a homozygous recessive dwarfing gene. If crossed to the aforementioned "pot-types", the resultant progeny returns to tall cut seedlings.

The Lillipots and Knight Series are seed crops. The Rocky Mountain and European pot varieties (cuttings) are no longer commercially available.

BRIEF DESCRIPTION OF ILLUSTRATION

The accompanying illustration shows typical specimens of the vegetative growth and flowers of the new variety depicted in color as nearly true as it is reasonably possible to make the same in a color illustration of this character. Although propagation by side shoot cuttings is described, other known methods of asexual reproduction may also be used to reproduce 'CFPC Cotillion'.

DESCRIPTION OF THE NEW VARIETY

The following is a detailed description of my new variety, with color terminology in accordance with the Royal Horticultural Society Colour Chart (RHSCC). The terminology used in color description herein refers to plate numbers in the aforementioned color chart. Color designations and color descriptions may deviate from the stated values depending upon varying environmental, seasonal and cultural conditions.

The information provided herein is based on observations of plants grown inside commercial greenhouses at Salinas, Calif. The height of plant and flower and foliage size are established as an average using standard commercial cultural practices. Where terms such as average, normal, ordinary, etc., are used, the characteristics so described are not considered distinguishing.

Name: CFPC Cotillion.

Classification:

*Botanical.*—*Dianthus caryophyllus.*

*Commercial.*—Carnation, dwarf pot type.

Parentage:

*Female parent.*—Unnamed seedling (No. 910149).

*Male parent.*—Unnamed seedling (No. 910116).

Plant:

*Height.*—About 6½-inches.

*Growing habit.*—Herbaceous, semi-upright, pot type.

*Blooming habit.*—As a spray.

*Blooming season.*—Year round.

*Rooting time.*—About 13 days.

*Mutation prone.*—No.

*Disease resistance.*—Good.

*Temperature tolerance.*—About 120° F. to 10° F.

*Breaking action.*—Good, about 7 on average.

Foliage:

*Color.*—Upper side: Near 137A. Lower side: Near 137D.

*Size.*—About 3-inches.

*Quantity.*—Numerous.

*Shape.*—Lanceolate.

*Texture.*—Smooth.

*Ribs.*—Central, Keeled.

*Arrangement.*—Bi-lateral along stem.

*Stem color.*—Green.

Bud:

*Shape.*—Oval.

*Color.*—Green.

*Length.*—About 1-inch.

*Diameter.*—About ⅓-inch.

Calyx:

*Number of sepals.*—About 5.

*Length.*—About 1-inch.

*Width.*—About ⅓-inch.

*Color.*—Outside — near 141B. Inside — near 145A.

Bloom:

*Shape.*—Round.

*Size.*—Diameter average: About 1½-inches. Depth average: About 1-inch.

*Borne.*—As a spray.

*Color.*—General tonality: Pink, picotee wine-red. Upper side: 56C with near 64B at edge. Lower side: Near 56D. Center: Near 56C. Outer petals: Near 56D.

*Keeping quality.*—3 to 4 weeks on plant.

*Fragrance.*—Slight.

Petals:

*Number.*—About 38.

*Outer petals.*—Length: About ¾-inch. Width: About 1-inch.

*Central petals.*—Length: About ½-inch. Width: About ½-inch.

*Texture.*—Smooth.

*Form.*—Fan shaped.

*Appearance.*—Shiny.

Reproductive organs:

*Stamens.*—None.

*Anthers.*—None.

*Filaments.*—None, lacks male reproductive organs.

*Pistil.*—Number: About 2 to 3. Color: White. Length: About ¼-inch.

*Stigma.*—Number: About 2 to 3. Color: Near 155D.

*Ovary.*—Shape: Conical, ribbed. Color: Base — green. Body — green. Apex — tan.

*Fertility.*—Female — average. Male — sterile.

I claim:

1. A new and distinct dwarf variety of carnation plant named 'CFPC Cotillion' substantially as shown and described.

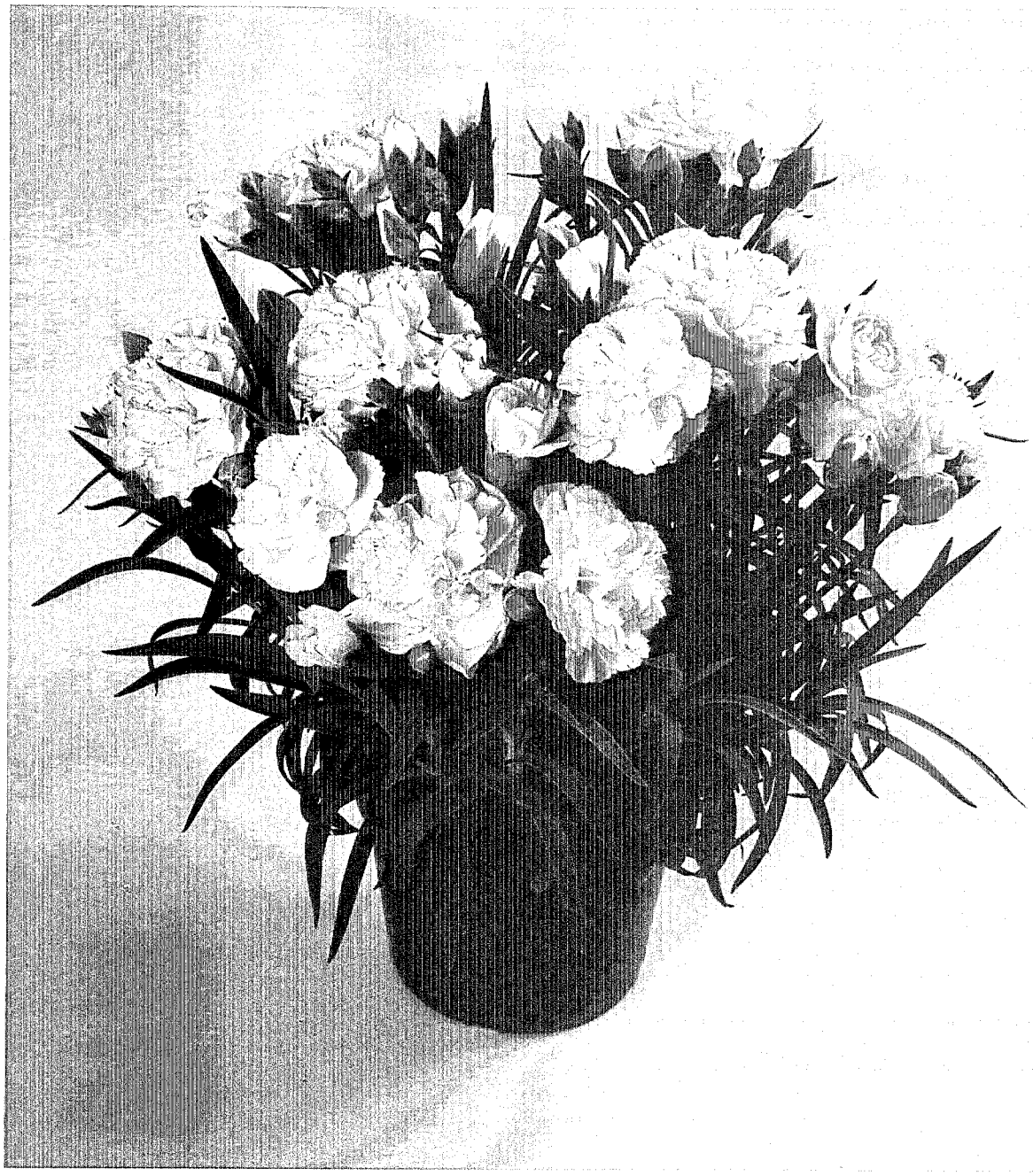

* * * * *